United States Patent [19]

Bettarini et al.

[11] Patent Number: 5,366,991
[45] Date of Patent: Nov. 22, 1994

[54] PYRAZOLECARBOXAMIDES EXHIBITING INSECTICIDE AND ACARICIDE ACTIVITY

[75] Inventors: Franco Bettarini; Luigi Capuzzi; Piero La Porta, all of Novara; Sergio Massimini, Milan; Franca Reggiori, Novara; Giovanni Meazza, Saronno, all of Italy

[73] Assignee: Eni Chem Synthesis S.p.A., Palermo, Italy

[21] Appl. No.: 127,622

[22] Filed: Sep. 27, 1993

[51] Int. Cl.$^5$ .................. A01N 43/56; C07D 231/14
[52] U.S. Cl. .................................. 514/406; 548/379.1
[58] Field of Search .................... 548/374.1; 514/406

[56] References Cited

FOREIGN PATENT DOCUMENTS 0289879 11/1988 European Pat. Off. .
0307801  3/1989 European Pat. Off. .
0365925  5/1990 European Pat. Off. .

OTHER PUBLICATIONS

Beilstein Handbuch der Organischen Chemie, vol. 12, Chapter III (no date available).
Atti Giornate Fitopatologiche, 1992.
Bulletin de la Societe Chimie de France, vol. 22, 1967.
Farmaco Ed. Sci., 1967 (Abstract).
JP 2101064 (Abstract) Database WPI, Week 9021, Derwent Publications Ltd., GB (1990).
JP 3063262 (Abstract) Database WPI, Week 9117, Derwent Publications Ltd., GB (1991).
JP 3206079 (Abstract) Database WPI, Week 9142, Derwent Publications Ltd., GB (1991).

Primary Examiner—Robert W. Ramsuer
Attorney, Agent, or Firm—Rogers & Wells

[57] ABSTRACT

5-pyrazolecarboxylic acid amide-based insecticide and acaricide compounds of general formula (I):

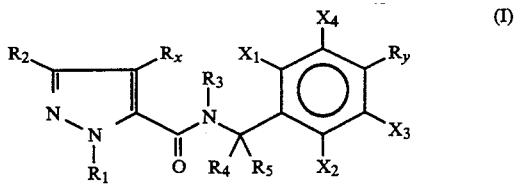

in which:
  $R_1$ represents a hydrogen atom, a linear or branched $C_1$–$C_4$ alkyl group or a benzyl group;
  $R_2$ represents a hydrogen atom or a linear or branched $C_1$–$C_4$ alkyl group;
  $R_x$ represents a hydrogen atom, a halogen atom such as chlorine, fluorine or bromine, or a linear or branched $C_1$–$C_4$ alkyl or haloalkyl group; or $R_2$ and $R_x$ together represent an RHC—(CH$_2$)$_n$—CH$_2$ group in which R represents a hydrogen atom or a $C_1$–$C_3$ alkyl group and n is a whole number between 1 and 2;
  $R_3$, $R_4$, $R_5$ represent, each independently, a hydrogen atom or linear or branched $C_1$–$C_4$ alkyl group;
  $X_1$, $X_2$, $X_3$ and $X_4$ represent, each independently, a hydrogen atom or a halogen atom such as chlorine, fluorine or bromine;
  $R_y$ represents a linear or branched $C_3$–$C_6$ haloalkoxyhaloalkoxy or haloalkoxyhaloalkylthio group, a linear or branched $C_1$–$C_6$ haloalkylthio group, a linear or branched $C_2$–$C_6$ haloalkenyl group or a linear or branched $C_3$–$C_6$ haloalkoxyhaloalkenyl group.

8 Claims, No Drawings

PYRAZOLECARBOXAMIDES EXHIBITING INSECTICIDE AND ACARICIDE ACTIVITY

This invention relates to compounds based on amides of 5-pyrazolecarboxylic acids.

More specifically, the invention relates to 5-pyrazolecarboxylic acid amide-based compounds exhibiting high insecticide and acaricide activity, a process for their preparation and their use in the agricultural, civil and livestock field for controlling damaging insects and mites.

European patent applications Nos. 289,879, 307,801, 329,020, 365,925, 405,808 and 462,573 describe 5-pyrazolecarboxylic acid amides exhibiting insecticide and acaricide activity. However the compounds described in the cited European patent applications have only limited insecticide activity. In this respect, as described in "Atti Giornate Fitopatologiche", 1992, vol. 1, pp. 29–36, the most representative term of the class, namely N-(4-tertbutylbenzyl)-4-chloro-3-ethyl-1-methylpyrazole-5-carboxamide, known as Tebufenpirad and corresponding to compound No. 51 of European patent application No. 289,879, is effective essentially as an acaricide and exhibits only limited insecticide activity. The present applicant has now found that by modifying the benzyl group bonded to the amide nitrogen atom with suitable halogenated substituents, compounds are obtained which, besides maintaining high acaricide activity, exhibit a surprisingly high insecticide activity, higher than that of the described pyrazolecarboxyamides of the known art.

The present invention therefore provides 5-pyrazolecarboxylic acid amide-based compounds of general formula (I):

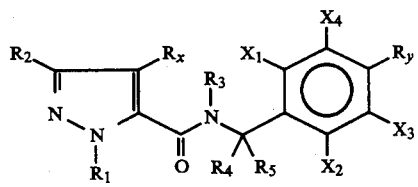

in which:
- $R_1$ represents a hydrogen atom, a linear or branched $C_1$–$C_4$ alkyl group or a benzyl group;
- $R_2$ represents a hydrogen atom or a linear or branched $C_1$–$C_4$ alkyl group;
- $R_x$ represents a hydrogen atom, a halogen atom such as chlorine, fluorine or bromine, or a linear or branched $C_1$–$C_4$ alkyl or haloalkyl group; or $R_2$ and $R_x$ together represent an

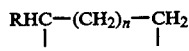

group in which R represents a hydrogen atom or a $C_1$–$C_3$ alkyl group and n is a whole number between 1 and 2;
- $R_3$, $R_4$, $R_5$ represent, each independently, a hydrogen atom or a linear or branched $C_1$–$C_4$ alkyl group;
- $X_1$, $X_2$, $X_3$ and $X_4$ represent, each independently, a hydrogen atom or a halogen atom such as chlorine, fluorine or bromine;
- $R_y$ represents a linear or branched $C_3$–$C_6$ haloalkoxyhaloalkoxy haloalkoxyhaloalkylthio group, a linear or branched $C_1$–$C_6$ haloalkylthio group, a linear or branched $C_2$–$C_6$ haloalkenyl group or a linear or branched $C_3$–$C_6$ haloalkoxyhaloalkenyl group.

The compounds of general formula (I) exhibit high insecticide and acaricide activity.

Examples of compounds of general formula (I) interesting for their insecticide and acaricide activity are: N-[3-chloro-4-(2-trifluoromethoxy-1,1,2-trifluoro-ethoxy)benzyl]-4-chloro-3-ethyl-1-methylpyrazole-5-carboxamide; N-[3-chloro-4-(2-trifluoromethoxy-1,1,2-trifluoroethoxy)benzyl]-4-chloro-1,3-dimethylpyrazole-5-carboxamide; N-[4-(2-trifluoro-methoxy-1,1,2-trifluoroethoxy) benzyl]-4-chloro-3-ethyl-1-methyl-pyrazole-5-carboxamide; N-[4-(2-trifluoromethoxy-1,1,2-trifluoro-ethoxy)benzyl]-4-chloro-1,3-dimethyl-pyrazole-5-carboxamide; N-[3-chloro-4-(2-pentafluoro-ethoxy-1,1,2-trifluoroethoxy)benzyl]-4-chloro-3-ethyl-1-methylpyrazole-5-carboxamide; N-[3-chloro-4-(2-heptafluoropropoxy-1,1,2-trifluoroethoxy)benzyl]-4-chloro-3-ethyl-1-methylpyrazole-5carboxamide; N-[3-fluoro-4-(2-trifluoro-methoxy-1,1,2-trifluoroethoxy)-benzyl]-4-chloro-3-ethyl-1-methyl-pyrazole-5-carboxamide; N-[3-fluoro-4-(2-trifluoromethoxy-1,1,2-trifluoro-ethoxy)benzyl]-4-chloro-1,3-dimethylpyrazole-5-carbox-amide; N-[2-chloro-4-(2-trifluoromethoxy-1,1,2-trifluoro-ethoxy)benzyl]-4-chloro-3-ethyl-1-methyl-pyrazole-5-carboxamide; N-[2-chloro-4-(2-trifluoromethoxy-1,1,2-trifluoroethoxy)benzyl]-4-chloro-1,3-dimethylpyrazole-5carboxamide; N-[2-fluoro-4-(2-trifluoromethoxy-1,1,2-trifluoroethoxy)benzyl]-4-chloro-3-ethyl-1-methylpyrazole-5-carboxamide; N-[2-fluoro-4-(2-trifluoromethoxy-1,1,2-trifluoroethoxy)benzyl]-4-chloro- 1,3-dimethylpyrazole-5-carboxamide; N-[3,5-dichloro-4-(2-trifluoromethoxy-1,1,2-trifluoroethoxy)-benzyl]-4-chloro-3-ethyl-1-methylpyrazole-5-carboxamide; N-[3,5-dichloro-4-(2-trifluoromethoxy-1,1,2-trifluoroethoxy)benzyl]-4-chloro-1,3-dimethylpyrazole-5-carboxamide; N-[4-(2-trifluoromethoxy-1,1,2-trifluoroethylthio)-benzyl]-4-chloro-3-ethyl-1-methylpyrazole-5carboxamide; N-[4-(2-trifluoromethoxy-1,1,2-trifluoroethylthio) benzyl]-4-chloro-1,3-dimethylpyrazole-5-carboxamide; N-[4-(2-trifluoromethoxy-1,1,2-trifluoroethoxy)benzyl]-4-bromo-3-ethyl-1-methylpyrazole-5-carboxamide; N-[3-chloro-4-(2-trifluoromethoxy-1,1,2-trifluoro-ethoxy)benzyl]-1,3-dimethylpyrazole-5-carboxamide. The present invention also provides a process for preparing compounds of general formula (I).

The compounds of general formula (I) can be obtained by a process comprising reacting a 5-pyrazolecarboxylic acid derivative of general formula (II):

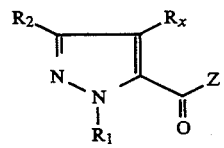

in which $R_1$, $R_2$ and $R_x$ have the aforesaid meaning, Z represents a halogen atom such as chlorine or bromine, a hydroxy group or a linear or branched $C_1$–$C_4$ alkoxy group, with a benzylamine of general formula (III):

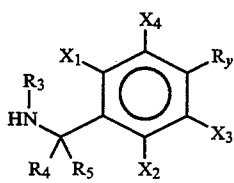

(III)

in which $R_3$, $R_4$, $R_5$, $X_1$, $X_2$, $X_3$, $X_4$ and $R_y$ have the aforesaid meanings.

The reaction can be conducted in the presence or absence of base and in the presence or absence of a solvent.

If Z represents a chlorine or bromine atom, the reaction is preferably conducted in the presence of an inorganic or organic base and in the presence of an inert organic solvent, at a temperature of between )° C. and the boiling point of the reaction mixture (solvent plus the base and the two aforesaid reagents). Examples of inorganic bases which can be used in the present process are sodium hydroxide, potassium hydroxide, sodium carbonate, potassium carbonate etc.

Examples of organic bases are pyridine, triethylamine etc. Examples of inert organic solvents are benzene, toluene, xylene, acetone, methylethyl ketone, chloroform, methylene chloride, ethyl acetate, ethyl ether, tetrahydrofuran, dioxane, acetonitrile, N,N-dimethylformamide, N-methylpyrrolidone, dimethylsulphoxide etc.

If Z represents a hydroxyl or alkoxy group the reaction is preferably conducted in the absence of a base. In this case the reaction can be conducted either in the absence or in the presence of a high-boiling solvent such as N,N-dimethylformamide, N-methylpyrrolidone, dimethylsulphoxide etc. at a temperature of between 150° C. and 250° C.

The 5-pyrazolecarboxylic acid derivatives of general formula (II) are known in the literature and can be prepared for example as described in "Bulletin de la Societé Chimie de France", 1966, page 293; "Farmaco Ed. Sc.", vol. 22, 1967, page 692 and in "Annalen der Chemie", vol. 598, 1956, page 186.

The benzylamines of general formula (III) can be prepared by known organic synthesis methods, such as described for example in "Beilstein Handbuch der Organischen Chemie", vol. 12, chapter III, page 2343.

The compounds of general formula (I) according to the present invention exhibit high insecticide and acaricide activity against insect and mite adults, larvae and eggs dangerous in the agricultural, civil and livestock fields.

In particular, the compounds of general formula (I) are active against important species of Coleoptera (*Leptinotarsa decemlineata, Callosobruchus chinensis* etc.), Hemiptera (*Macrosiphum euphorbiae, Myzus persicae, Psylla piri* etc.), Diptera (Aedes Aegypti, *Musca domestica* etc.), Lepidoptera (*Spodoptera littoralis, Chilo supressalis* etc.), Tetranychidae (*Tetranychus urticae, Panonychus ulmi, Panonychus citri* etc.), Eriophyidae (*Phytoptus avellanae, Eriophyes vitis, Eriophyes piri* etc.), and Tarsonemidae (*Steneotarsonemus pallidus* etc.). At the same time, the compounds of general formula (I) have low toxicity against many useful insects and mites, mammals, fish, amphibia and birds, and do not exhibit phytotoxicity. Because of their positive characteristics they can be advantageously used to protect agricultural and horticultural crops, domestic and farm animals and environments frequented by man against harmful insects and mites.

For practical use in agriculture and other sectors it is often advantageous to use compositions of insecticide and acaricide activity containing one or more compounds of general formula (I) as active substance.

Compositions can be used in the form of dry powders, wettable powders, emulsifiable concentrates, microemulsions, pastes, granulates, solutions, suspensions etc. The choice of composition type depends on the specific use.

The compositions are prepared by known methods, for example by diluting or dissolving the active substance with a solvent medium and/or a solid diluent, possibly in the presence of surfactants. Suitable solid inert diluents or supports include kaolin, alumina, silica, talc, bentonire, chalk, quartz, dolomite, attapulgite, montmorillonite, diatomaceous earth, cellulose, starch etc. Suitable liquid inert diluents include, in addition to water, organic solvents such as aromatic hydrocarbons (xylols or alkyl benzoyl mixtures), aliphatic hydrocarbons (hexane, cyclohexane), chloro aromatics (chlorobenzene), alcohols (methanol, propanol, butanol, octanol), esters (isobutyl acetate), ketones (acetone, cyclohexanone, acetophenone, isophorone, ethylamylketone), or vegetable or mineral oils, or their mixtures etc.

Suitable surfactants include wetting agents and emulsifiers of non-ionic type (polyethoxylated alkylphenols, polyethoxylated fatty alcohols etc.), anionic type (alkylbenzenesulphonates, alkylsulphonates etc.) and cationic type (quaternary alkylammonium salts, etc.).

Dispersants (such lignin and its salts, cellulose derivatives, alginates etc.) and stabilizers (such as antioxidants, ultraviolet absorbants etc.) can also be added.

To widen the range of action of said compositions, other active ingredients such as other insecticides or acaricides, herbicides, fungicides or fertilizers can be added to them.

The active substance concentration in said compositions can vary within a wide range, depending on the active compound, the application for which they are intended, the environmental conditions and the type of formulation used.

In general the active substance concentration is between 1% and 90% and preferably between 10% and 40%.

The dose to be applied also varies depending on various factors such as the type and degree of infestation, the type of composition used, and climatic and environmental factors. For practical agricultural uses, compound doses of between 50 g and 500 g per hectare provide sufficient protection.

The following examples illustrate the present invention without however representing a limitation thereto.

EXAMPLE 1

Preparation of N-[3-chloro-4-(2-trifluoromethoxy-1,1,2-trifluoroethoxy)-benzyl]-4-chloro-3-ethyl-1-methylpyrazole-5-carboxamide (Compound No. 1)

A mixture consisting of 2 ml of methylene chloride, 0.11 ml of triethylamine and 250 mg of 3-chloro-4-(2-trifluoromethoxy-1,1,2-trifluoroethoxy)-benzylamine (0.77 moles) is slowly added dropwise to a solution of 166 mg (0.8 mmoles) of 4-chloro-3-ethyl-1-methyl-5-pyrazolecarboxylic acid chloride in 3 ml of methylene chloride. The solution obtained is maintained under agitation at ambient temperature for 5 hours.

It is then diluted with 10% hydrochloric acid solution, extracted with ethyl ether, the organic phase washed with a saturated sodium bicarbonate solution, dried and concentrated.

The crude product obtained is purified by silica gel chromatography eluting with hexane/ethyl acetate in a ratio of 8:2.

250 mg of Compound No. 1 are obtained with a melting point of 63°–64° C.

$^1$H-NMR (CDCl$_3$): δ at 1.2 (t, 3H); 2.6 (q, 2H); 4.1 (s, 3H); 4.5 (d, 2H); 5.9 (dt, 1H); 7.0–7.5 (complex, 4H).

EXAMPLE 2

Preparation of N-[3-chloro-4-(2-trifluoromethoxy-1,1,2-trifluoroethoxy)-benzyl]-4-chloro-1,3-dimethylpyrazole-5-carboxamide (Compound No. 2)

A mixture consisting of 2 ml of methylene chloride, 0.10 ml of triethylamine and 250 mg of 3-chloro-4-((2-trifluoromethoxy-1,1,2-trifluoroethoxy)-benzylamine (0.65 moles) is slowly added dropwise to a solution of 133 mg (0,69 mmoles) of 4-chloro-1,3-dimethyl-5-pyrazolecarboxylic acid chloride in 3 ml of methylene chloride. The solution obtained is maintained under agitation at ambient temperature for 5 hours.

It is then diluted with 10% hydrochloric acid solution, extracted with ethyl ether, the organic phase washed with a saturated sodium bicarbonate solution, dried and concentrated.

The crude product obtained is purified by silica gel chromatography eluting with hexane/ethyl acetate in a ratio of 8:2.

200 mg of Compound No. 2 are obtained with a melting point of 73°–74° C.

$^1$H-NMR (CDCl$_3$): δ at 2.4 (s, 3H); 4.2 (s, 3H); 4.6 (d, 2H); 6.0 (dt, 1H); 7.0–7.7 (complex, 4H).

EXAMPLE 3

Preparation of N-[4-(2-trifluoromethoxy-1,1,2-trifluoroethoxy) benzyl]-4-chloro-3-ethyl-1-methylpyrazole-5-carboxamide (Compound No. 3)

A mixture consisting of 4 ml of methylene chloride, 0.22 ml of triethylamine and 450 mg of 4-((2-trifluoromethoxy-1,1,2-trifluoroethoxy)-benzylamine (1.56 moles) is slowly added dropwise to a solution of 332 mg (1.6 mmoles) of 4-chloro-3-ethyl-1-methyl-5-pyrazolecarboxylic acid chloride in 6 ml of methylene chloride. The solution obtained is maintained under agitation at ambient temperature for 4 hours.

It is then diluted with 10% hydrochloric acid solution, extracted with ethyl ether, the organic phase washed with a saturated sodium bicarbonate solution, dried and concentrated.

The crude product obtained is purified by silica gel chromatography eluting with hexane/ethyl acetate in a ratio of 8:2.

490 mg of Compound No. 3 are obtained with a melting point of 54° C.

$^1$H-NMR (CDCl$_3$): δ at 1.2 (t, 3H); 2.55 (q, 2H); 4.1 (s, 3H); 4.5 (d, 2H); 5.9 (dt, 1H); 6.8–7.4 (complex, 5H).

EXAMPLE 4

Operating in accordance with the procedure described in examples 1–3, the following compounds were prepared: N-[3,5-dichloro-4-(2-trifluoromethoxy-1,1,2-trifluoroethoxy) benzyl]-4-chloro-3-ethyl-1-methyl-pyrazole-5-carboxamide (Compound No. 4): M.P. 67°–68° C.

$^1$H-NMR (CDCl$_3$): δ at 1.2 (t, 3H); 2.55 (q, 2H); 4.0 (s, 3H); 4.5 (d, 2H); 6.1 (dt, 1H); 7.2 (bt, 1H); 7.3 (s, 2H). N-[3,5-dichloro-4-(2-trifluoromethoxy-1,1,2-trifluoroethoxy) benzyl]-4-chloro-1,3-dimethylpyrazole-5-carboxamide (Compound No. 5): M.P. 84°–85° C.

$^1$H-NMR (CDCl$_3$): δ at 2.2 (s, 3H); 4.1 (s, 3H); 4.55 (d, 2H); 6.1 (dt, 1H); 7.15 (bt, 1H); 7.35 (s, 2H). N-[4-(2-trifluoromethoxy-1,1,2-trifluoroethylthio)benzyl]-4-chloro-3-ethyl-1-methylpyrazole-5-carboxamide (Compound No. 6): M.P. 72°–73° C.

$^1$H-NMR (CDCl$_3$): δ at 1.2 (t, 3H); 2.6 (q, 2H); 4.1 (s, 3H); 4.65 (d, 2H); 5.8 (dt, 1H); 7.1 (bt, 1H); 7.4 (d, 2H); 7.65 (d, 2H). N-[4-(2-trifluoromethoxy-1,1,2-trifluoroethylthio)benzyl]-4-chloro-1,3-dimethylpyrazole-5-carboxamide (Compound No. 7): M.P. 75°–76° C.

$^1$H-NMR (CDCl$_3$): δ at 2.2 (s, 3H); 4.1 (s, 3H); 4.65 (d, 2H); 7.1 (bt, 1H); 7.4 (d, 2H); 7.65 (d, 2H). (Z)-N-[4-(2-chloro-3,3,3-trifluoroprop-1-enyl)benzyl]-4-chloro-3-ethyl-1-methylpyrazole-5-carboxamide (Compound No. 8): M.P. 90°–91° C.

$^1$H-NMR (CDCl$_3$): δ at 1.2 (t, 3H); 2.6 (q, 2H); 4.1 (s, 3H); 4.65 (d, 2H); 7.1 (bt, 1H); 7.25 (s, 1H); 7.4 (s, 2H); 7.75 (s, 2H). N-[2-chloro-4-(2-trifluoromethoxy-1,1,2-trifluoro-ethoxy)benzyl]-4-chloro-3-ethyl-1-methyl-pyrazole-5-carboxamide (Compound No. 9): M.P. 64°–650° C.

$^1$H-NMR (CDCl$_3$): δ at 1.2 (t, 3H); 2.6 (q, 2H); 4.1 (s, 3H); 4.7 (d, 2H); 5.9 (dt, 1H); 7.1 (m, 1H); 7.3 (bs, 2H); 7.5 (d, 1H). N-[4-(2-heptafluoropropoxy-1,1,2-trifluoroethoxy)benzyl]-4-chloro-3-ethyl-1-methylpyrazole-5-carboxamide (Compound No. 10): M.P. 80°–81° C.

$^1$H-NMR (CDCl$_3$): δ at 1.2 (t, 3H); 2.6 (q, 2H); 4.1 (s, 3H); 4.6 (d, 2H); 6.15 (dt, 1H); 7.1 (bt, 1H); 7.2–7.5 (complex, 3H). 5 N-[4-(1,1,2,2-tetrafluoroethylthio)benzyl]-4-chloro-3-ethyl-1-methylpyrazole-5-carboxamide (Compound No. 11): M.P. 85°–86° C.

$^1$H-NMR (CDCl$_3$): δ at 1.2 (t, 3H); 2.6 (q, 2H); 4.1 (s, 3H); 4.65 (d, 2H); 5.75 (tt, 1H); 7.1 (bt, 1H); 7.4 (d, 2H); 7.65 (d, 2H). N-[4-(2-trifluoromethoxy-1,1,2-trifluoroethoxy)benzyl]-2,6-dimethyl-2,4,5,6-tetrahydrocyclopentapyrazole-3-carboxamide (Compound No. 12).

$^1$H-NMR (CDCl$_3$): δ at 1.2 (t, 3H); 2.0 (m, 1H); 2.6 (m, 3H); 3.1 (m, 1H); 4.2 (s, 3H); 4.6 (d, 2H); 5.9 (dt, 1H); 6.8–7.5 (complex, 5H). N-[3-chloro-4-(2-trifluoromethoxy-1,1,2-trifluoro-ethoxy)benzyl]-2,6-dimethyl-2,4,5,6-tetrahydrocyclopentapyrazole-3-carboxamide (Compound No. 13).

$^1$H-NMR (CDCl$_3$): δ at 1.2 (d, 3H); 2.0 (m, 1H); 2.6 (m, 3H); 3.1 (m, 1H); 4.2 (s, 3H); 4.6 (d, 2H); 6.0 (dt, 1H); 7.1 (bt, 1H); 7.2–7.5 (complex, 3H). N-[3,5-dichloro-4-(2-trifluoromethoxy-1,1,2-trifluoroethoxy) benzyl]-2,6-dimethyl-2,4,5,6-tetrahydrocyclopentapyrazole-3-carboxamide (Compound No. 14).

$^1$H-NMR (CDCl$_3$): δ at 1.2 (d, 3H); 2.0 (m, 1H); 2.6 (m, 3H); 3.1 (m, 1H); 4.2 (s, 3H); 4.6 (d, 2H); 6.1 (dt, 1H); 7.2 (bt, 7.35 (s, 2H).

EXAMPLE 5

Determination of insecticide and acaricide activity:

a) Insecticide activity against Leptinotarsa decemlineata larvae (L.D.; Coleoptera)

Potato plants are infested with ten 5-day old Leptinotarsa decemlineata larvae and then immersed in a 10 vol % acetone-in-water dispersion of acetone of the product under examination (Compounds Nos. 1-3), also containing Tween 20 (0.05%). The percentage mortality is determined 48 hours after treatment, in comparison with potato plant-infesting larvae immersed in a 10% acetone-in-water solution (reference).

b) Acaricide activity against tetranychus urticae adults (T.U.; tetranychidae)

Discs formed from bean leaves are infested with Tetranychus urticae adult females and then sprayed with a 10 vol% acetone-in-water dispersion of acetone of the product under examination (Compound Nos. 1-3), also containing Tween 20 (0.05%). The percentage mortality is determined 48 hours after treatment, in comparison with disc-infesting mites sprayed only with a 10% acetone-in-water solution (reference).

Table 1 shows the results of the determinations. These results are expressed as percentage mortality of insects and mites treated with Compounds Nos. 1-3 under examination at the doses indicated. Table 1 also shows the results obtained for the reference compound (RC) corresponding to N-(4-tert-butylbenzyl)-4-chloro-3-ethyl-1-methylpyrazole-5-carboxamide (Compound No. 51 of European patent application No. 289,879).

TABLE 1

| Compound | L.D. (larvae) 10 ppm | T.U. (adults) 10 ppm |
|---|---|---|
| 1 | 100 | 100 |
| 2 | 100 | 100 |
| 3 | 30 | 100 |
| 4 | 100 | 100 |
| 6 | 100 | 100 |
| 7 | 80 | 100 |
| 8 | 100 | 100 |
| RC | 0 | 100 |

We claim:

1. 5-pyrazolecarboxylic acid amide-bused compounds of general formula (I):

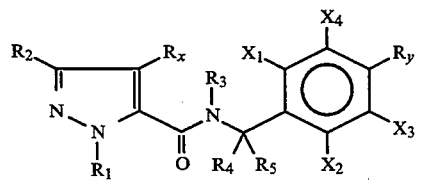

in which:

$R_1$ represents a hydrogen atom, a linear or branched $C_1-C_4$ alkyl group or a benzyl group;

$R_2$ represents a hydrogen atom or a linear or branched $C_1-C_4$ alkyl group;

$R_x$ represents a hydrogen atom, a halogen, atom or a linear or branched $C_1-C_4$ alkyl or haloalkyl group; or $R_2$ and $R_x$ together represent an

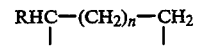

group in which R represents a hydrogen atom or a $C_1-C_3$ alkyl group and n is a whole number between 1 and 2;

$R_3$, $R_4$, $R_5$ represent, each independently, a hydrogen atom or a linear or branched $C_1-C_4$ alkyl group;

$X_1$, $X_2$, $X_3$ and $X_4$ represent, each independently, a hydrogen atom or halogen atom;

$R_y$ represents a linear or branched $C_3-C_6$ haloalkoxyhaloalkoxy or haloalkoxyhaloalkylthio group, or a linear or branched $C_3-C_6$ haloalkoxyhaloalkenyl group.

2. An insecticide or acaricide as claimed in claim 1, consisting of N-[3-chloro-4-(2-trifluoromethoxy-1,1,2-trifluoroethoxy)benzyl]-4-chloro-3-ethyl-1-methylpyrazole-5-carboxamide.

3. An insecticide or acaricide as claimed in claim 1, consisting of N-[3-chloro-4-(2-trifluoromethoxy-1,1,2-trifluoroethoxy)benzyl]-4-chloro-1,3-dimethylpyrazole-5-carboxamide.

4. An insecticide or acaricide as claimed in claim 1, consisting of N-[4-(2-trifluoromethoxy-1,1,2-trifluoroethoxy) benzyl]-4-chloro-3-ethyl-1-methyl-pyrazole-5-carboxamide.

5. An insecticide or acaricide as claimed in claim 1, consisting of N-[3,5-dichloro-4-(2-trifluoromethoxy-1,1,2trifluoroethoxy)benzyl]-4-chloro-3-ethyl-1-methylpyrazole-5carboxamide.

6. An insecticide or acaricide as claimed in claim 1, consisting of N-[4-(2-trifluoromethoxy-1,1,2-trifluoroethylthio) benzyl]-4-chloro-3-ethyl-l-methyl-pyrazole-5-carboxamide.

7. Compositions exhibiting insecticide and acaricide activity containing one or more compounds in accordance with claim 1, either alone or in the presence of solid supports, liquid diluents, surfactants or other active principles.

8. Compositions exhibiting insecticide and acaricide activity as claimed in claim 7, wherein the active substance concentration is between 1% and 90%.

* * * * *

UNITED STATES PATENT AND TRADEMARK OFFICE
CERTIFICATE OF CORRECTION

PATENT NO.   : 5,366,991
DATED        : November 22, 1994
INVENTOR(S)  : Franco Bettarini, Luigi Capuzzi, Piero LaPorta, Franca Reggiori and Giovanni Meazza It is certified that error appears in the above-indentified patent and that said Letters Patent is hereby corrected as shown below:

On title page, item
  [73] Assignee: Ministero Dell 'Universita' E Della Ricerca Scientifica E Tecnologica Signed and Sealed this Twenty-third Day of July, 1996

*Attest:*

BRUCE LEHMAN

*Attesting Officer*    *Commissioner of Patents and Trademarks*